US008696556B2

(12) United States Patent
Ibrahim et al.

(10) Patent No.: US 8,696,556 B2
(45) Date of Patent: Apr. 15, 2014

(54) TISSUE RETRACTORS WITH FLUID EVACUATION/INFUSION AND/OR LIGHT EMISSION CAPABILITY

(75) Inventors: Tamer Ibrahim, Pleasant Hill, CA (US); Michael J. Banchieri, Discovery Bay, CA (US)

(73) Assignee: Endoscopic Technologies, Inc., San Ramon, CA (US)

( * ) Notice: Subject to any disclaimer, the term of this patent is extended or adjusted under 35 U.S.C. 154(b) by 1266 days.

(21) Appl. No.: 12/510,500

(22) Filed: Jul. 28, 2009

(65) Prior Publication Data
US 2011/0028792 A1  Feb. 3, 2011

(51) Int. Cl.
A61B 1/32  (2006.01)

(52) U.S. Cl.
USPC ........................................................ 600/205

(58) Field of Classification Search
USPC .................................. 600/201–206, 210–216
See application file for complete search history.

(56) References Cited

U.S. PATENT DOCUMENTS

| | | | |
|---|---|---|---|
| 3,584,822 A | 6/1971 | Oram | |
| 4,048,987 A | 9/1977 | Hurson | |
| 4,562,832 A * | 1/1986 | Wilder et al. | 600/223 |
| 4,949,927 A | 8/1990 | Madocks et al. | |
| 5,348,259 A | 9/1994 | Blanco et al. | |
| 5,368,592 A | 11/1994 | Stern et al. | |
| 5,624,381 A | 4/1997 | Kieturakis | |
| 5,727,569 A | 3/1998 | Benetti et al. | |
| 5,755,660 A * | 5/1998 | Tyagi | 600/205 |
| 5,885,271 A | 3/1999 | Hamilton et al. | |
| 5,899,425 A | 5/1999 | Corey et al. | |
| 6,217,589 B1 | 4/2001 | McAlister | |
| 6,254,532 B1 | 7/2001 | Paolitto et al. | |
| 6,278,057 B1 | 8/2001 | Avellanet | |
| 6,361,493 B1 | 3/2002 | Spence et al. | |
| 6,379,297 B1 | 4/2002 | Furnish et al. | |
| 6,383,134 B1 * | 5/2002 | Santilli | 600/205 |
| 6,464,629 B1 | 10/2002 | Boone et al. | |
| 6,506,149 B2 | 1/2003 | Peng et al. | |
| 6,537,212 B2 * | 3/2003 | Sherts et al. | 600/205 |
| 6,565,508 B2 | 5/2003 | Scirica et al. | |
| 6,589,166 B2 * | 7/2003 | Knight et al. | 600/205 |
| 6,758,808 B2 | 7/2004 | Paul et al. | |
| 6,860,668 B2 | 3/2005 | Ibrahim et al. | |
| 6,974,411 B2 | 12/2005 | Belson | |
| 6,994,669 B1 | 2/2006 | Gannoe et al. | |
| 7,018,328 B2 | 3/2006 | Mager et al. | |

(Continued)

FOREIGN PATENT DOCUMENTS

| | | |
|---|---|---|
| EP | 0167345 | 1/1986 |
| FR | 1255099 | 3/1961 |
| WO | WO-01/50946 A3 | 7/2001 |

OTHER PUBLICATIONS

Office Action Dated Nov. 1, 2011 in related U.S. Appl. No. 12/433,801.

(Continued)

*Primary Examiner* — Anu Ramana
*Assistant Examiner* — Michael Araj
(74) *Attorney, Agent, or Firm* — Henricks, Slavin & Holmes LLP

(57) ABSTRACT

Retractor apparatus including a blade and a fluid port and/or a light emitter associated with blade, and surgical systems including an arm and a retractor apparatus.

29 Claims, 8 Drawing Sheets

(56) References Cited

U.S. PATENT DOCUMENTS

| | | |
|---|---|---|
| 7,041,055 B2 | 5/2006 | Young et al. |
| 7,150,714 B2 * | 12/2006 | Myles .......................... 600/205 |
| 7,399,272 B2 | 7/2008 | Kim et al. |
| 7,794,387 B2 | 9/2010 | Olson et al. |
| 2002/0161277 A1 | 10/2002 | Boone et al. |
| 2004/0015047 A1 | 1/2004 | Mager et al. |
| 2005/0152739 A1 | 7/2005 | Ibrahim et al. |
| 2005/0215851 A1 | 9/2005 | Kim et al. |
| 2005/0226682 A1 | 10/2005 | Chersky et al. |
| 2007/0123747 A1 | 5/2007 | Boone et al. |
| 2007/0225568 A1 | 9/2007 | Colleran |
| 2008/0139879 A1 | 6/2008 | Olson et al. |
| 2008/0281150 A1 | 11/2008 | Wright |
| 2010/0280325 A1 | 11/2010 | Ibrahim et al. |
| 2010/0317925 A1 | 12/2010 | Banchieri et al. |

OTHER PUBLICATIONS

Office Action Dated May 18, 2011 in related U.S. Appl. No. 12/433,801.

Office Action Dated Aug. 2, 2011 in related U.S. Appl. No. 12/483,863.

* cited by examiner

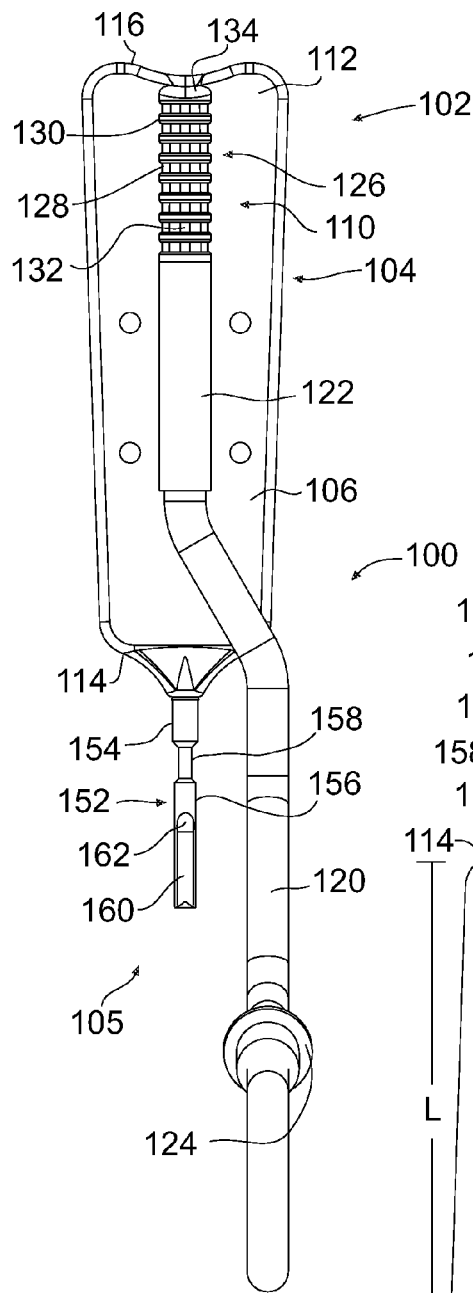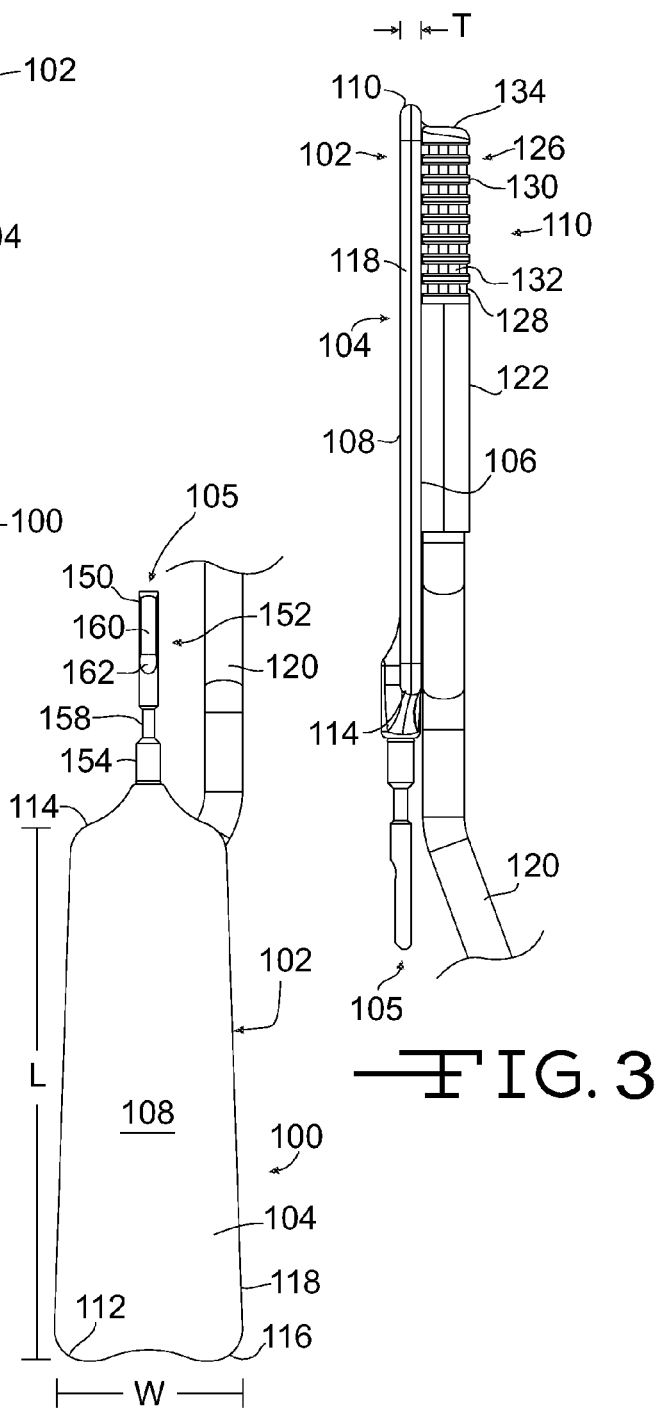
FIG. 2
FIG. 3
FIG. 4

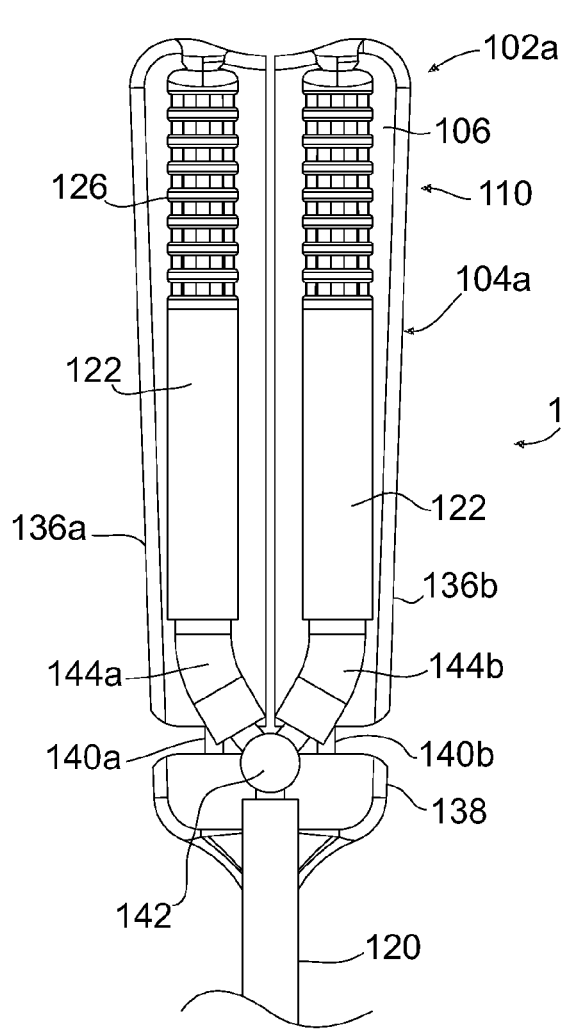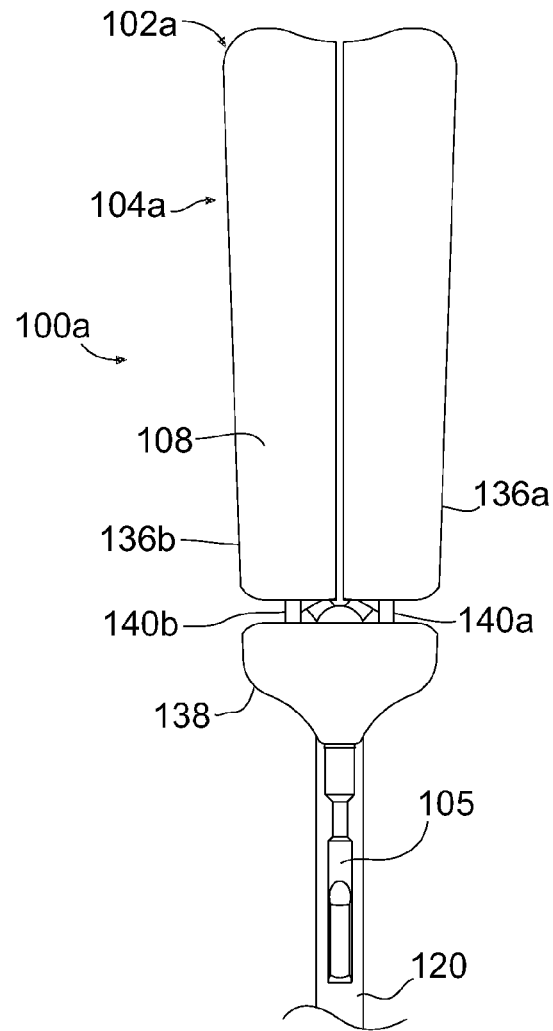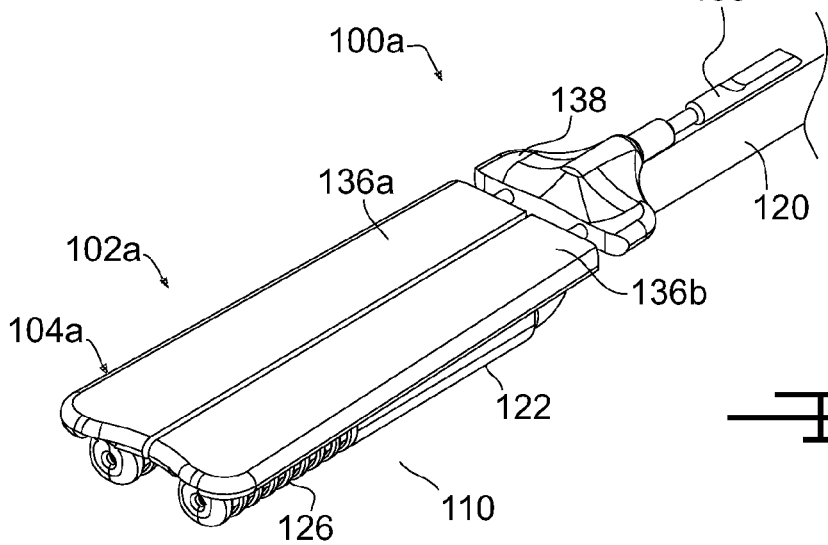

TISSUE RETRACTORS WITH FLUID EVACUATION/INFUSION AND/OR LIGHT EMISSION CAPABILITY

BACKGROUND

1. Field

The present inventions relate generally to tissue retractors.

2. Description of the Related Art

Tissue retractors (or "retractors") are used in surgical procedures to stabilize, position, and/or inhibit the physiological movement of tissue. The retractors are carried on an arm, such as an articulating arm, a rigid arm, a malleable arm or the like, that allows the surgeon to fixedly position the retractor. By way of example, but not limitation, tissue retractors may be used in minimally invasive surgical procedures such as minimally invasive mitral valve surgery to repair or replace a mitral valve. Here, a pair of retractors are inserted into an incision that has been made in the left atrium, e.g. to the right of the right-most pulmonary vein when the patient is on his/her back. The retractors are used to spread the incision open, thereby providing access to the mitral valve.

The present inventors have determined that conventional tissue retractors are susceptible to improvement. For example, the present inventors have determined that blood or other fluids may be present within the target tissue structure and, in the exemplary context of minimally invasive mitral valve surgery, blood may pool on the floor of the left atrium. The present inventors have determined that additional arm-mounted structures that are used to illuminate a target area, such as the interior of the left atrium, can interfere with the procedure.

SUMMARY

A retractor apparatus in accordance with one implementation of a present invention includes a retractor, with a blade and a fluid port associated with the blade, and a connector configured to secure the retractor to a mechanical arm. Surgical systems in accordance with various implementations of at least some of the present inventions include an arm and a retractor, associated with the arm, which has a blade and a fluid port associated with the blade. Such apparatus and systems may be used to remove or infuse fluid, while retracting tissue, during a surgical procedure.

A retractor apparatus in accordance with one implementation of a present invention includes a retractor, with a blade configured to emit light, and a connector configured to secure the retractor to a mechanical arm. Surgical systems in accordance with various implementations of at least some of the present inventions include an arm and a retractor, associated with the arm, which has a blade that is configured to emit light. Such apparatus and systems may be used to illuminate a surgical site, while retracting tissue, during a surgical procedure.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 2 is a bottom view of a tissue retractor apparatus in accordance with one embodiment of a present invention.

FIG. 3 is a side view of the tissue retractor apparatus illustrated in FIG. 2.

FIG. 4 is a top view of the tissue retractor apparatus illustrated in FIG. 2.

FIG. 5 is a bottom view of a tissue retractor apparatus in accordance with one embodiment of a present invention.

FIG. 6 is a top view of the tissue retractor apparatus illustrated in FIG. 5.

FIG. 7 is a perspective view of the tissue retractor apparatus illustrated in FIG. 5.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
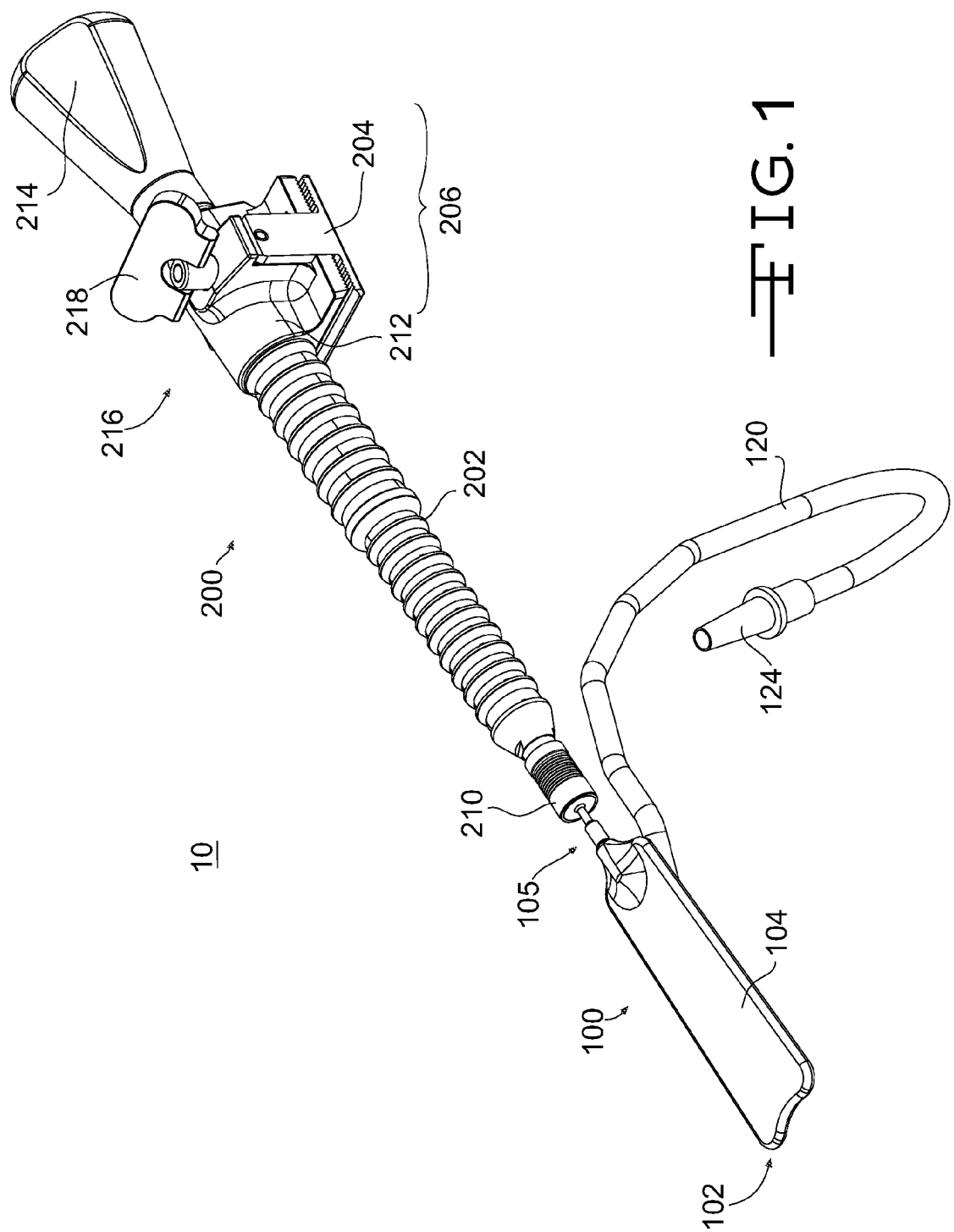
FIG. 1 is a perspective view of a surgical system in accordance with one embodiment of a present invention.
Figure 8:
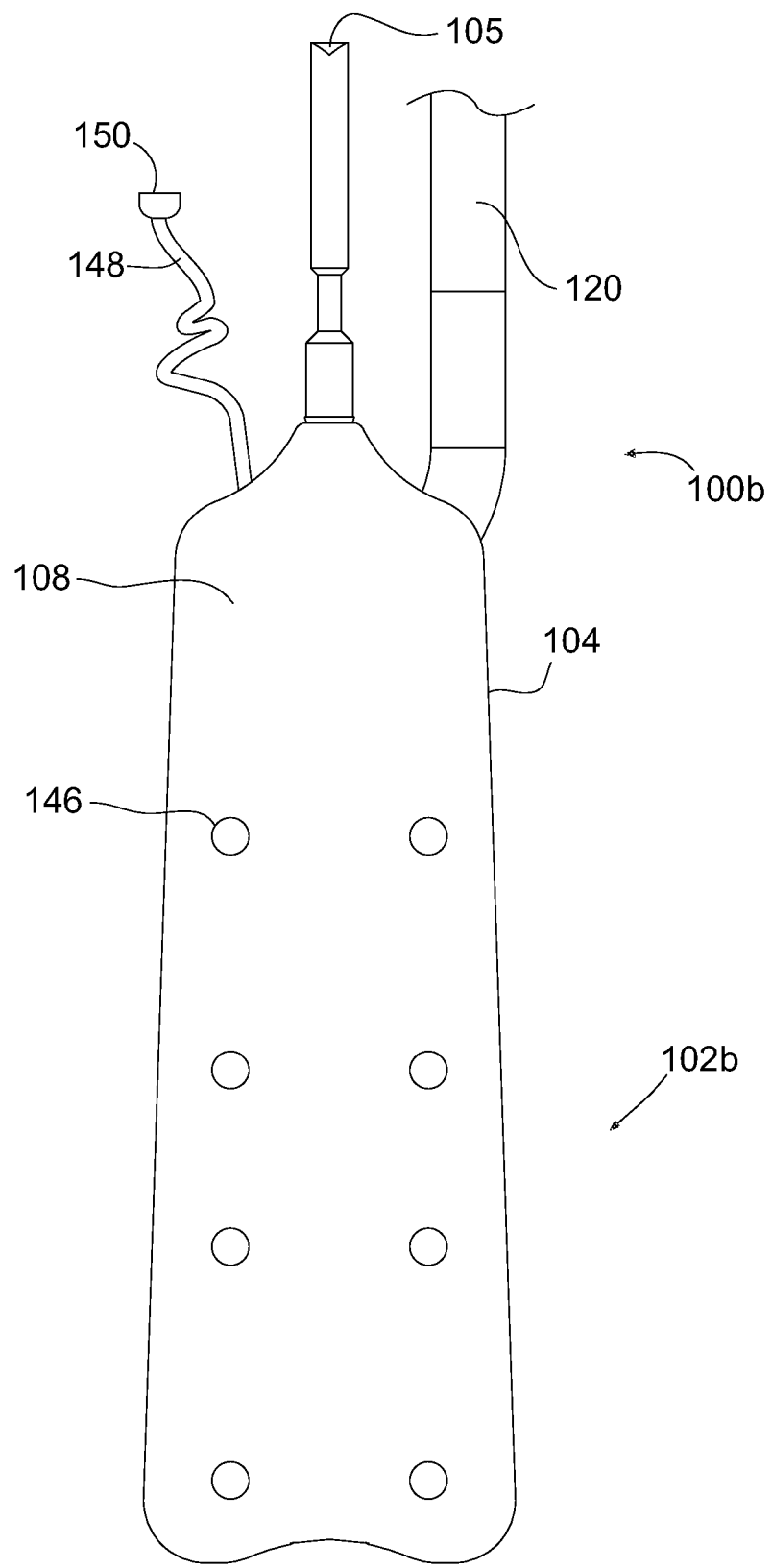
FIG. 8 is a top view of a tissue retractor apparatus in accordance with one embodiment of a present invention.

An exemplary surgical system in accordance with one embodiment of a present invention is generally represented by reference numeral 10 in FIG. 1. The surgical system includes a tissue retractor apparatus 100 carried on a flexible articulating arm (or "arm") 200. Exemplary tissue retractors apparatus, such as tissue retractor apparatus 100, which may be releasably or permanently coupled to the arm 200 or other arm, are discussed in greater detail below with reference to FIGS. 1-8. The exemplary arm 200 is discussed in greater detail below with reference to FIGS. 1 and 9-16C.

As illustrated for example in FIGS. 2-4, the exemplary tissue retractor apparatus 100 includes a retractor 102 and a connector 105 that may be used to releasably connect the retractor to, for example, the flexible articulating arm 200.

The retractor 102 includes a blade 104, which has a first (or "tissue engagement") surface 106 and a second surface 108 on the opposite side of the blade, and a fluid port 110 that may be used for suction or fluid infusion. Although not limited to any particular shape, the blade 104 is relatively long and narrow (FIGS. 2 and 4) as well as planar and thin (FIG. 3). The second surface 108 in the illustrated embodiment is a smooth surface, i.e. a surface that is not rough and that has no projections extending therefrom. So configured, the retractor 102 is a low profile device that facilitates visual and actual access to associate tissue structure. The exemplary blade 104 is also rigid in that it will hold its shape when exposed to the forces typically associated with a minimally invasive surgical procedure. In other implementations, the blade may be somewhat flexible. The corners 112 of the blade 104 are rounded at the proximal end 114 and distal end 116, as are the side edges 118, to reduce the likelihood of tissue trauma.

The exemplary fluid port 110 may be connected to a source of negative pressure or to a fluid source (not shown). In the embodiment illustrated in FIGS. 2-4, one end of a fluid tube 120 is secured to a connector tube 122 that is carried by the blade 104. A connector 124 may be mounted on other end of the fluid tube 120. The fluid port 110, whose location relative to the remainder of the retractor 102 varies depending on the intended application, may be formed in a variety of ways. In the illustrated embodiment, the fluid port 110 is defined by a grate 126 that includes a plurality of longitudinally extending ribs 128 and a plurality of substantially circular ribs 130 that together define openings 132. The proximal end of the grate 126 is open and connected to the connector tube 122, and the distal end is closed by a cap 134. The use of the grate 126 reduces the likelihood that there will be total occlusion of the fluid port 110 by tissue, especially when a vacuum force is applied to the fluid port. The distal end of the grate 126 may be located adjacent to the blade distal end 116, and the length of the grate may be about 15-50% of the length of the blade 104, in some implementations. Such positioning decreases the likelihood that portions of the grate 126 will be located outside the associated tissue structure (e.g. outside the left atrium) and exposed to air during the surgical procedure.

The fluid port 110 may, in other implementations, simply be the open distal end of the connector tube 122. Alternatively, the distal end of the connector tube 122 may be sealed and a plurality of longitudinally extending and/or transversely extending slots may be formed in the connector tube. In those instances where the connector tube 122 is omitted, the fluid tube 120 may be directly secured to the blade 104 and the fluid port 110 defined by the end of the fluid tube or a grate that is connected directly to the end of the fluid tube. Alternatively, the distal end of a fluid tube 120 that is secured to the blade may be sealed, and a plurality of longitudinally extending and/or transversely extending slots may be formed in the portion of the fluid tube associated with the retractor blade.

Another exemplary retractor apparatus is generally represented by reference numeral 100a in FIGS. 5-7. The retractor apparatus 100a is substantially similar to retractor apparatus 100 in form and functionality and similar elements are represented by similar reference numerals. Here, however, the retractor apparatus is also configured to provide lateral retraction. To that end, the retractor 102a includes a blade 104a with a pair of rigid blade members 136a and 136b that are respectively mounted to a blade base 138 with a pair of malleable rods 140a and 140b. The malleable rods 140a allow the blade members 136a and 136b to be moved relative to the blade base 138 and to one another. The malleable rods 140a and 140b are configured such that the blade 104a may be readily bent by the physician to a desired shape, without springing back when released, and will remain in that shape during the surgical procedure. The stiffness of the malleable rods 140a and 140b must be low enough to allow the blade 104a to be bent, but high enough to resist bending when the forces associated with a surgical procedure are applied to the blade.

Other implementations of the present retractor apparatus may be configured to provide adjustable malleable retraction in other ways. By way of example, but not limitation, the retractor may include a malleable internal structure (e.g. an annealed stainless steel structure) with a relatively soft, flexible outer structure (e.g. a molded plastic such as silicone). For example, instead of the rigid blade members 136a and 136b, base 138 and malleable rods 140a and 140b, a retractor blade similar to retractor blade 104a may be provided with an internal u-shaped malleable structure and an overmolded soft outer structure that includes a pair of blade members separated by a longitudinally extending gap similar to that shown in FIG. 6. The blade members may be integral with the blade base or, in a manner similar to that shown in FIG. 6, spaced from the base.

One or both of the blade members 136a and 136b may be provided with a fluid port. In the exemplary embodiment illustrated in FIGS. 5-7, each of the blade members 136a and 136b is provided with a fluid port 110, a connector tube 122 and a grate 126. The fluid tube 120 is connected to the connector tubes 122 by a y-adapter 142 and a pair of flexible intermediate tubes 144a and 144b (FIG. 5).

The blade members 136a and 136b may be identical in size and shape, as shown in FIGS. 5-7, or may be different in size and/or shape if required by a particular surgical application.

Retractor apparatus in accordance with at least some of the present inventions may also be configured to illuminate the surgical site. One example of such a retractor apparatus is generally represented by reference numeral 100b in FIG. 8. The retractor apparatus 100b is essentially identical to retractor apparatus 100 and similar elements are represented by similar reference numerals. Here, however, the retractor 102b is provided with a plurality of light emitters 146 that are carried by the blade 104. By way of example, but not limitation, the exemplary light emitters are carried on the second surface 108, i.e. the surface opposite the tissue engagement surface 106 and fluid port 110, in two rows. The light emitters 146 are also essentially flush with the second surface 108 (i.e. project less than 1 mm) so that the second surface remains smooth. The exemplary light emitters 146 are wide diffusion angle light emitting diodes ("LEDs"). The LED power wires (not shown), which may be molded into the blade 104, extend through a cable 148 to a connector 150. The connector 150 may be connected to a corresponding power connector on the associated arm (e.g. arm 200). In other implementations, the cable 148 may extend along the fluid tube 120.

It should be noted that the light emission function may be performed by structures other than LEDs. For example, other electrically based light emitter(s) (e.g. incandescent or fluorescent light emitters) or fiber optic light emitter(s) may be provided. Another alternative is to form the blade from phosphorescent material that will absorb light energy prior to being inserted into an atrium or other the tissue structure, store the energy, and emit visible light until the energy runs out.

The connector that releasably secures the tissue retractor apparatus 100-100b to the associated flexible articulating arm 200 (or other arm) may be any connector that is suitable for use with the corresponding connector 210 (discussed below) on the arm. In the illustrated embodiments, and referring to FIGS. 2 and 3, the connector 105 includes a shaft 152 with first and second end portions 154 and 156 connected to one another by an intermediate portion 158. The outer diameter of the intermediate portion 158 is less than that of the end portions 154 and 156 to enable the user to angle the tissue retractor relative to the connector 210 while maintaining a stable connection to the articulating arm 200. The second end portion 156 includes a channel 160 and a spherical indentation 162 that cooperate with the connector 210 in the manner described below with reference to FIGS. 15A-16C to allow the retractor apparatus 100-100b to be easily secured to, and removed from, the articulating arm 200 by hand during the course of normal use.

The connector 105 is but one example of a structure which performs the function releasably securing a tissue retractor to a corresponding connector on an arm, such as a flexible articulating arm or some other type of arm. Other exemplary structures which perform the function of releasably securing a tissue retractor to an arm include, but are not limited to, the following. A quick-connect, which is configured to be releasably connected to a corresponding structure (e.g. a cylindrical shaft) on the arm, may be provided on the tissue retractor apparatus. Alternatively, the arm may be provided with the quick-connect and the tissue retractor apparatus may be provided with a corresponding structure (e.g. a cylindrical shaft). In either case, the quick-connect may be configured such that the quick-connect collar slides distally or proximally to engage the post. The tissue retractor apparatus may be provided with a male (or female) threaded connector and the arm may be provided with a corresponding female (or male) threaded connector. The tissue retractor apparatus and/or the arm may be provided with a magnetic connector. The tissue retractor apparatus may be provided with a ball that is configured to be received by a collet on the arm, or the arm may be provided with a ball that is configured to be received by a collet on the tissue retractor apparatus. In either case, a cable or a rod may be used to retract the collet into the collar. The arm (or tissue retractor apparatus) may be provided with a hollow cylinder and set screw arrangement and the tissue retractor apparatus (or arm) may be provided with a shaft that is received within the cylinder. The arm (or tissue retractor apparatus) may be provided with a hollow cylinder that has one or more internal indentations and the tissue retractor apparatus (or arm) may be provided with a shaft that has one or more outwardly biased depressible members that fit into the indentations. The arm (or tissue retractor apparatus) may be provided with a chuck and the tissue retractor apparatus (or arm) may be provided with a shaft that is received within the chuck. The tissue retractor apparatus (or arm) may be provided with a shaft including one or more transverse notches and the arm (or tissue retractor apparatus) may be provided with a hollow cylinder that has one or more transverse holes. After the shaft is inserted into the hollow cylinder such that the notches are aligned with the holes, pins may be placed in the holes to prevent the shaft from moving.

The retractors described above may, in other implementations, be a permanent part of a surgical system such as, for example, surgical systems that include a flexible articulating arm, a rigid arm or a malleable arm. Here, the tissue retractor will be permanently connected to the arm through the use of instrumentalities, such as adhesive, weld(s) and/or screws or other mechanical fasteners, that do not allow the tissue retractor to be removed without disassembly or destruction of at least that portion of the system.

The dimensions of the present retractor apparatus will depend on the intended application. In some implementations configured for use in cardiac surgery, the blade 104 (or 104a) may be relatively long, narrow and thin. With respect to long and narrow, the ratio of length L to width W (FIG. 4) may be at least about 2 to 1 and, in various implementations, the ratio of length to width may range from about 3 to 1 to about 8 to 1. The thickness T (FIG. 3) may be about 20% of the width W or less.

In one implementation that is configured for use in cardiac surgery, the blade 104 (or 104a) is about 3.8 inches long and about 1.25 inches wide at its widest point. The thickness of the blade 104 (or 104a) is about 0.13 inch in areas not aligned with the connector tube 122 and is about 0.42 inch at the connector tube. In other implementations, the length of the blade 104 (or 104a) may range from about 2.5 inches to 4.5 inches, and the width of the blade 104 (or 104a) may range from about 0.5 inch to 2.0 inch. With respect to materials, the suitable materials for the retractor 102 and 102a include, but are not limited to rigid plastics such as polyethylene or metals such as stainless steel. The connector 105 may be formed by, for example, a metal (e.g. stainless steel) with a polyethylene overmold.

Turning to the other aspects of the exemplary surgical system 10 illustrated in FIG. 1, the flexible articulating arm 200 includes a linkage assembly 202, a bracket 204 that mounts the arm to the supporting structure (e.g. the side rail of an operating table), a tension block 206 that applies tension to the linkage assembly cable 208 (FIG. 9), and a connector 210 that releasably couples the tissue retractor apparatus 100 to the arm. The tension block 206 includes a mounting block 212 and a rotatable handle 214. The mounting block 212 may have an internal passage receiving a screw and, affixed to the screw, a transverse pin riding in slots formed in opposite sides of the mounting block. The pin and slots prevents the screw from rotating relative to mounting block 212. The threads of the screw engage internal threads in the rotatable handle 214, which also has an internal shoulder that can engage with the screw's head. The screw is directly attached (or otherwise operably connected to) the cable 208 and, accordingly, the handle 214 may be rotated to selectively increase or decrease the tension on the linkage assembly 202 to fix the orientation of the arm or permit repositioning of the arm. The bracket 204 and mounting block 212 may also be used to fix the location of the flexible articulating arm 200 on the supporting structure. To that end, a screw mechanism 216, including a pivot handle 218, may be used to drive the bracket 204 towards (and away from) mounting block 212.

Figure 9:
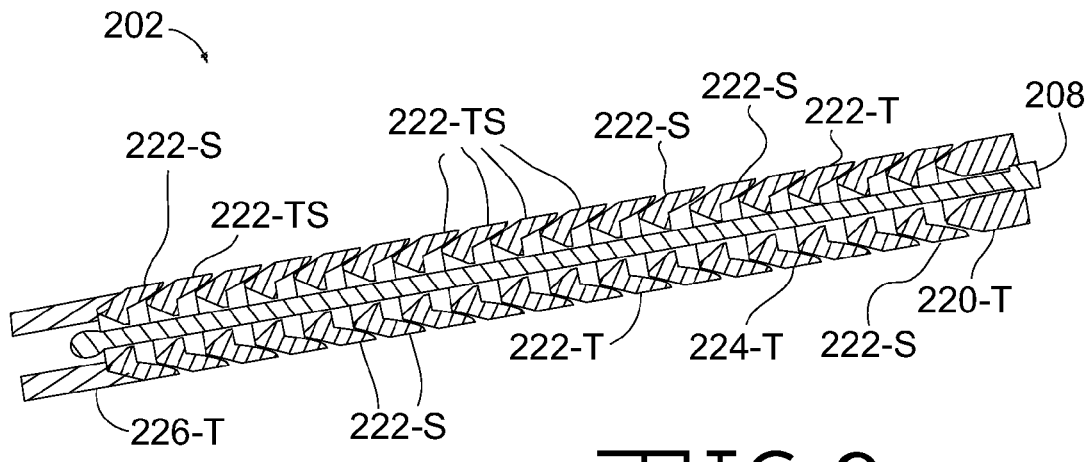
FIG. 9 is a section view of a linkage assembly in accordance with one embodiment of a present invention.
Figure 10:
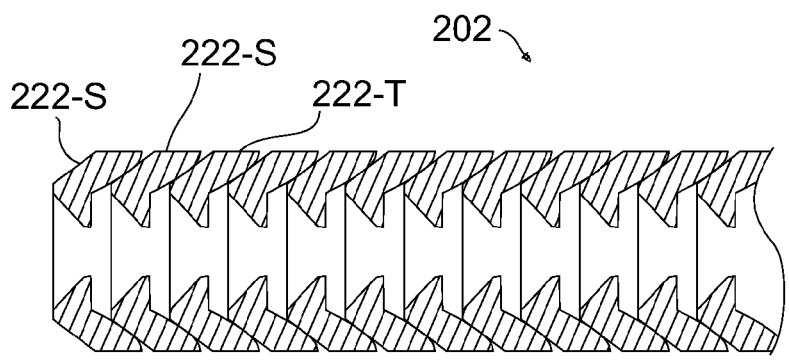
FIG. 10 is a section view of a portion of a linkage assembly in accordance with one embodiment of a present invention.

Turning to FIGS. 9 and 10, the exemplary linkage assembly 202 includes a number of differently shaped links 220, 222, 224 and 226. Each link includes at least one contact surface, which contact couples to a neighboring contact surface of another link. Links 220 and 226 each have exactly one contact surface. The contact surface of link 220 is convex, while the contact surface of link 226 is concave. Links 222 and 224 each have two contact surfaces, one concave and the other convex. At one longitudinal end of the linkage assembly 202, link 226 is coupled with a link 222, while link 220 is coupled with a link 222 at the other longitudinal end. The tension cable 208 extends through the links and is anchored within link 226. An alternative linkage assembly 202a is illustrated in FIGS. 11, 12A and 12B and described in greater detail below.

The exemplary links may be formed from various metals and/or combinations thereof and the reference characters associated with each link include a material indicator. More specifically, a "-T" indicates that a link is composed primarily of titanium and a "-S" indicates that a link is composed primarily of stainless steel. With respect to links that employ two or more distinct metallic compounds, e.g. one for each contact surface, a "-TS" indicates that a link has a concave surface primarily composed of a titanium alloy, and a convex surface primarily composed of a stainless steel alloy, while a "-ST" indicates that a link has a concave surface primarily composed of a stainless steel alloy, and a convex surface primarily composed of a titanium alloy.

In the exemplary linkage assembly 202 illustrated in FIGS. 9 and 10, the concave and convex surfaces of the exemplary links 220, 222, 224 and 226 embody shapes, which for their materials, maximize static friction as well as kinetic friction when contacting each other under tension. In some implementations, a first link with a first contact surface (e.g. link 222-T) is composed of a first contact material and a second link with a second contact surface (e.g. link 222-S) is composed of a second contact material, with each of the contact materials primarily composed of a different metallic compound. A high friction coupling between the first link and the second link may created by the first contact surface contacting the second contact surface when induced by the tension cable 208. The first contact surface, composed of the first contact material, contacting the second contact surface, composed of the second contact material, has a higher friction coefficient than results from composing both contact surfaces of either contact material. Suitable friction coefficients may range from, but are not limited to, 0.3 to 0.3875.

Figure 11:
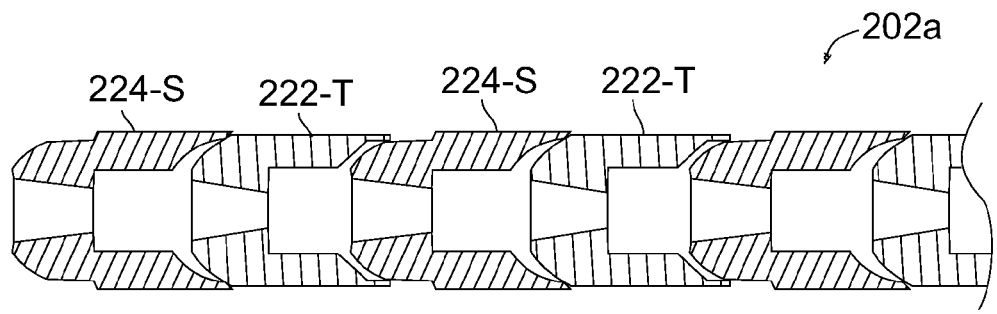
FIG. 11 is a section view of a portion of a linkage assembly in accordance with one embodiment of a present invention.
Figure 12A:
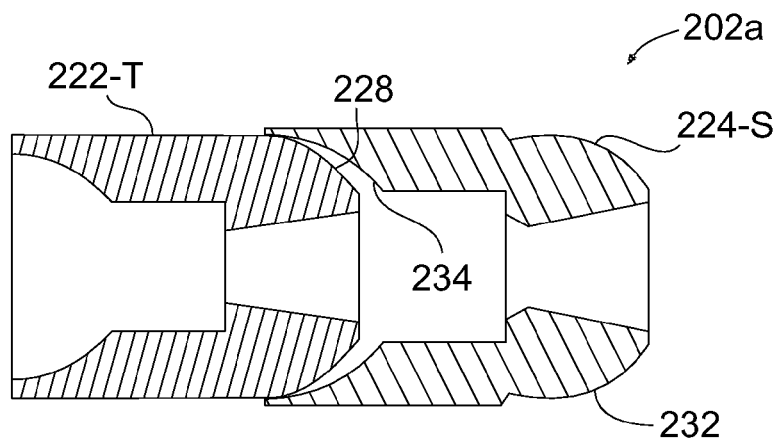
FIGS. 12A and 12B are section views of links in accordance with one embodiment of a present invention.
Figure 12B:
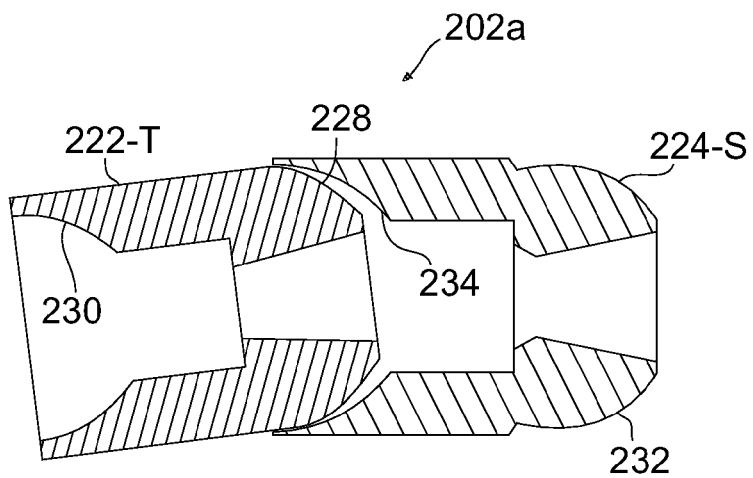

Turning to FIGS. 12A-12B, in the linkage assembly 202a illustrated in FIG. 11, at least two of the links (i.e. links 222-T and 224-S) are coupled through a spherical convex surface contacting a spherical concave surface. The spherical convex surface 228 connects with the semi-spherical concave surface 234. The diameters of the two surfaces are preferably slightly different, with the convex semi-spherical 228 diameter being larger than the semi-spherical diameter of the interfacing concave surface 234. Convex surface 228 and concave surface 234 form an interference fit when the two surfaces contact each other under tension. The wall of link 224-S is sufficiently thin and resilient where the two surfaces come together to provide an area contact between the links.

Figure 12C:
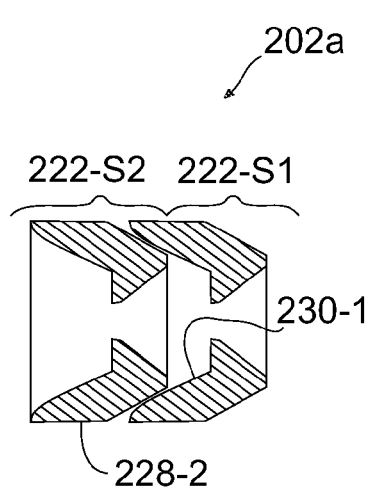
FIGS. 12C and 12D are section views of links in accordance with one embodiment of a present invention.

FIG. 12C shows two stainless steel links (labeled 222-S1 and 222-S2) from the exemplary linkage assembly illustrated in FIG. 9 coupled with a spherical convex surface contacting a conical concave surface. More specifically, the spherical convex surface 228-2 connects with the conical concave surface 230-1. The diameters of the two surfaces are slightly different, with the convex semi-spherical 228-2 diameter being larger than the conical diameter of the interfacing concave surface 230-1. Convex surface 228-2 and concave surface 230-1 form an interference fit when the two surfaces contact each other under tension. The wall of link 222-S1 is sufficiently thin and resilient where the two surfaces come together to provide an area of contact.

Figure 12D:
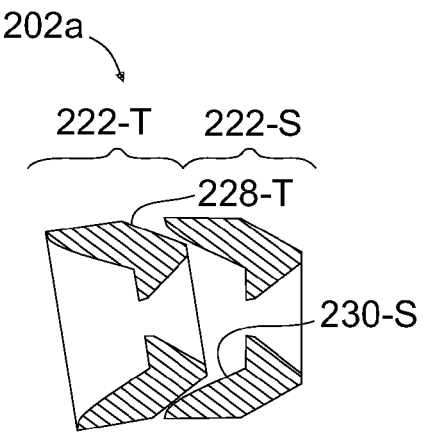

In FIG. 12D, links 222-T and 222-S from the exemplary linkage assembly illustrated in FIG. 9 form a coupling where a spherical convex titanium surface contacts a conical concave stainless steel surface, i.e. the spherical convex surface 228-T connects with the conical concave surface 230-S. The diameters of the two surfaces are slightly different, with the convex semi-spherical 228-T diameter being larger than the conical diameter of the interfacing concave surface 230-S. Convex surface 228-T and concave surface 230-S form an interference fit when the two surfaces contact each other under tension. The wall of link 222-S is sufficiently thin and resilient where the two surfaces come together to provide an of area contact.

The circular edge of the opening of each link illustrated in FIGS. 12A-12D may be concentric with the center of the imaginary sphere in which the surface lies when the links are fully engaged with each other. The edge is rounded to avoid a sharp edge that could damage the tensioning cable. The rounded edge has a very small radius of curvature to maximize the contact area of the mating convex and concave surfaces. The fact that the edge is rounded instead of sharp has negligible effect on the contact area.

The diameters of the convex and mating concave link surfaces may vary over the length of the linkage assembly. This supports the need for increased strength and/or stiffness at the proximal end of the articulating arm near the tension block 206, where the applied mechanical moment is greatest. The joints at the proximal end of the arm are preferably larger in diameter. This increases their rotational inertia, or resistance to rotation, in addition to providing greater frictional contact area than smaller distal beads located furthest from tension block 206. The greatest load-bearing link is frequently the most proximal link. This link may be sunk into the body of the articulating column providing a mechanical lock, prohibiting rotation of this link.

One potential mode of failure of a flexible articulating arm that is used repeatedly is cable failure. If the cable fails in an arm with a single uniform cable, nothing is left holding the links together. This allows the links to fall into the surgical field. A variety of factors are associated with the potential for cable failure. The cable (e.g. cable 208) is shortened during use to create compressive forces between adjacent links and rigidify the linkage assembly, which results in tensile fatigue forces being applied to the cable. Shear forces are applied to the strands in contact with the inner radius of the links. If these radii are small, they contact a finite area of the cable and act as a knife edge, greatly wearing a localized area of the cable as it slides over these edges. If the arm is forcefully moved when in the rigid state (when all the slack is already removed from the cable), large loads will stretch the cable strands and greatly accelerate failure.

Various portions of the links may be configured so as to reduce the likelihood of cable failure. For example, the radius of curvature of areas contacting the cable may be increased, as alluded to above. The bend radius of a linkage assembly may be selected based on the minimum radius of curvature permissible for the cable that will be used in conjunction with that linkage assembly. The shape of the adjacent links may be designed to provide a gentle contour creating the selected radius, thereby more evenly distributing the load to more of the cable strands and minimizing contact forces applied to the strands in contact with the links and any sharp edges thereof.

Figure 13A:
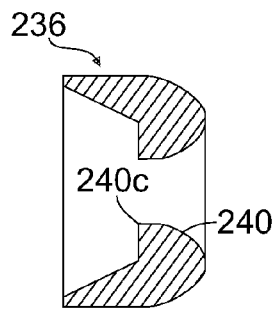
FIGS. 13A and 13B are section views of links in accordance with one embodiment of a present invention.
Figure 13B:
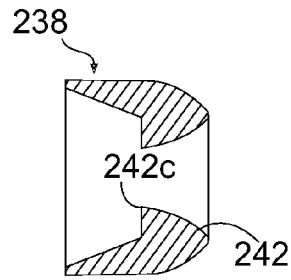
Figure 13C:
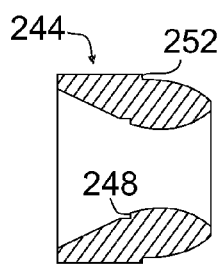
FIGS. 13C and 13D are section views of links in accordance with one embodiment of a present invention.
Figure 13D:
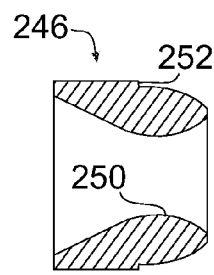
Figure 13E:
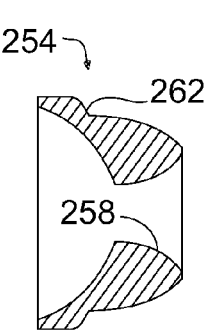
FIGS. 13E and 13F are section views of links in accordance with one embodiment of a present invention.
Figure 13F:
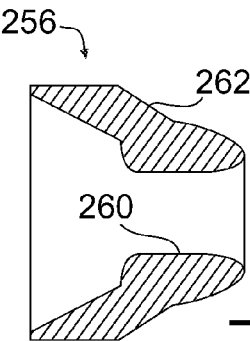
Figure 14:
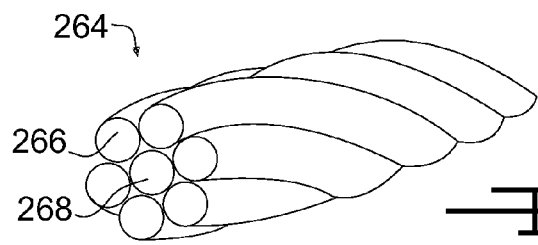
FIG. 14 perspective view of a portion of a cable in accordance with one embodiment of a present invention.

The links illustrated in FIGS. 13A-13F are examples of links that may be employed in the present linkage assemblies to reduce the likelihood of cable failure. Referring first to FIGS. 13A and 13B, links 236 and 238 include inner surfaces 240 and 242 that each have a relatively large radius of curvature. The inner surface corners 240c and 242c may also be rounded in some implementations. The links 244 and 246 illustrated in FIGS. 13C and 13D include inner surfaces 248 and 250 that each have a relatively large radius of curvature. The links 244 and 246 also have an external ridge 252 that prevents the arm assembly from bending beyond a preset limit. The links 254 and 256 illustrated in FIGS. 13E and 13F include inner surfaces 258 and 260 that each have a relatively large radius of curvature. The links 254 and 256 also have an external ridge 262 that prevents the arm assembly from bending beyond a preset limit. The external ridge 262 is more tapered than that illustrated in FIGS. 13C and 13D to provide a smoother external profile of the arm assembly.

Decreasing the coefficient of friction between cable and link contact surfaces also improves the life of the cable. A thin, biocompatible material may be used to provide a hard and lubricious surface. With no surface treatment, the cable may catch on the internal surface of the links causing large contact forces and strains on portions of the cable. The lubricious surface allows the cable to more easily slide along the surfaces of the links as tension is applied, thereby reducing the chance of larger point load or frictional wear on the cable. One option for the lubricious surface is hard chrome plating. The chrome is hard and lubricious, and thus serves as a good material for plating if the desired result is wear resistance. The links, the cable or both may be coated to provide this advantage.

In other implementations, the cable may include a device that will hold the links together despite cable failure. One example of such a cable is generally represented by reference numeral 264 in FIG. 14. The cable 264 includes a plurality of stainless steel strands 266 and at least one elastic (or superelastic) strand 268. When the strands 266 fail, the elastic nature of the strand 268 will cause that portion of the cable 264 to stretch and allow the flexible arm to fail while still holding the links together. One suitable material for the elastic strand 268 is a nickel titanium alloy sold under the trade name Nitinol.

Figure 15A:
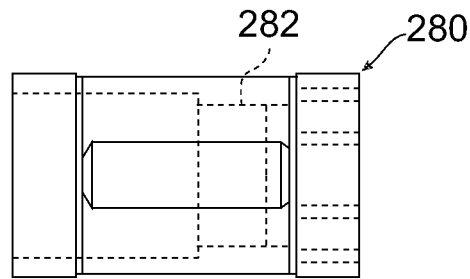
FIG. 15A is a plan view of a connector collar in accordance with one embodiment of a present invention.
Figure 15C:
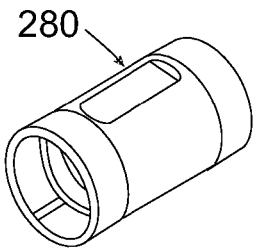
FIG. 15C is a perspective view of the connector collar illustrated in FIG. 15A.
Figure 15B:
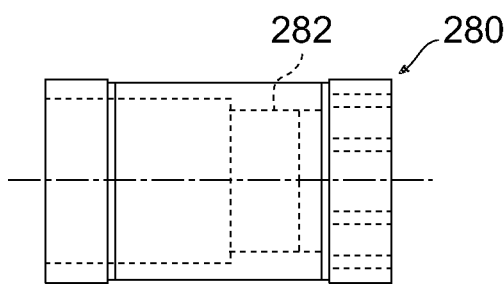
FIG. 15B is another plan view of the connector collar illustrated in FIG. 15A.
Figure 16A:
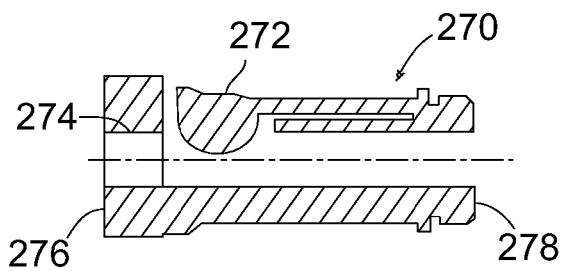
FIG. 16A is a section view of a connector inner cylinder in accordance with one embodiment of a present invention.
Figure 16C:
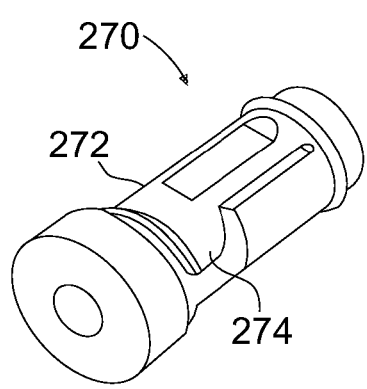
FIG. 16C is a perspective view of the connector inner cylinder illustrated in FIG. 16A.
Figure 16B:
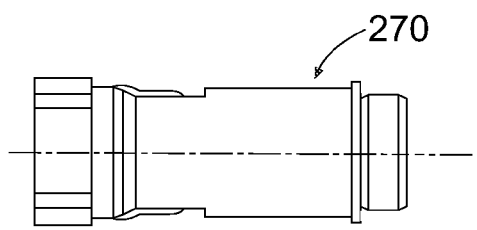
FIG. 16B is a plan view of the connector inner cylinder illustrated in FIG. 16A.

With respect to the manner in which the tissue retractor apparatus 100 releasably connected the flexible articulating arm 200 in the illustrated implementation, the exemplary connector 210 (FIG. 1) may be a two-part structure including the outer collar illustrated in FIGS. 15A-15C and the inner cylinder illustrated in FIGS. 16A-16C.

Referring first to FIGS. 16A-16C, the inner cylinder 270 includes a deflectable portion 272, which creates a spring effect, and a spherical surface 274 that is carried by the deflectable portion and is configured to slide along shaft channel 156 and mate with the shaft detent 158 (FIG. 4). Inner cylinder end 276 is secured to the associated arm, and the shaft 148 is inserted at end 278. The collar 280 is movable between a locked position which prevents movement of the shaft 148 and an unlocked position which permits withdrawal of the shaft, and is biased to the locked position by an internal coil spring (not shown). The collar 280 (FIGS. 15A-15C) also includes a necked down portion 282. To insert the tissue retractor shaft 148, collar 280 is moved away from cylinder end 276 until the collar 280 is in the unlock position where the neck down portion 282 does not apply force to the deflectable portion 272. After the shaft 148 is inserted and the spherical surface 274 of the deflectable portion 272 mates with the spherical concave detent 226, the collar 280 may be released. The spring (not shown) forces the collar 280 back to the lock position, where the neck down portion 282 comes into contact with the deflectable portion 272, forcing the spherical surface 274 to seat in the shaft detent 158, and locking the axial and rotational position of the tissue retractor apparatus. Suitable materials for the inner cylinder 270 and collar 280 include stainless steel.

Additional details concerning the exemplary flexible articulating arms described above, as well as other arms, are provided in U.S. Pat. No. 6,860,668 and U.S. Patent Pub. No. 2005/0226682 A1, which are incorporated herein by reference.

Although the inventions disclosed herein have been described in terms of the preferred embodiments above, numerous modifications and/or additions to the above-described preferred embodiments would be readily apparent to one skilled in the art. By way of example, but not limitation, the present inventions includes the surgical systems described above and below in combination with a source of negative pressure or fluid. It is intended that the scope of the present inventions extend to all such modifications and/or additions and that the scope of the present inventions is limited solely by the claims set forth below.

We claim:
1. A retractor apparatus, comprising:
a retractor including
a longitudinally extending blade having a tissue contact side and a second side opposite the tissue contact side, and
a fluid port carried by, extending longitudinally along and projecting outwardly from the tissue contact side of the blade, the fluid port including a grate, with a plurality of longitudinally extending ribs and a plurality of ribs that cross the longitudinally extending ribs, that defines a plurality of openings that face in different directions; and
a connector associated with the retractor and configured to secure the retractor to a mechanical arm.
2. A retractor apparatus as claimed in claim 1, further comprising:
a fluid tube; and
a connector tube having a first end connected to the fluid tube and second end associated with the fluid port.
3. A retractor apparatus as claimed in claim 1, wherein the blade is substantially rigid and flat.
4. A retractor apparatus as claimed in claim 1, wherein the blade include first and second blade members; and
the first and second blade members are movable relative to one another.
5. A retractor apparatus as claimed in claim 4, wherein the fluid port comprises a first fluid port associated with the first blade member and a second fluid port associated with the second blade member.
6. A retractor apparatus as claimed in claim 1, further comprising:
at least one light emitting element carried by the blade.
7. A retractor apparatus as claimed in claim 1, wherein the connector is configured to releasably secure the retractor to the mechanical arm.
8. A retractor apparatus as claimed in claim 7, wherein the connector includes a shaft with a spherical indentation.
9. A retractor apparatus, comprising:
a retractor including
a blade with a blade base, first and second blade members that are movable relative to one another, and first and second malleable rods that respectively connect the first and second blade members to the blade base, and
a fluid port associated with the blade; and
a connector associated with the retractor and configured to secure the retractor to a mechanical arm.
10. A retractor apparatus as claimed in claim 9, wherein the fluid port comprises first and second fluid ports that are respectively associated with the first and second blade members.
11. A retractor apparatus as claimed in claim 10, wherein the first and second fluid ports are carried by and project outwardly from the first and second blade members.
12. A retractor apparatus as claimed in claim 11, wherein the first and second fluid ports each include a grate.
13. A retractor apparatus as claimed in claim 9, wherein the first and second blade members are substantially rigid and flat.
14. A surgical system, comprising:
an arm; and
a retractor, operably connected to the arm, including a longitudinally extending blade having a tissue contact side and a second side opposite the tissue contact side, and a fluid port projecting outwardly from the tissue contact side of the blade, the fluid port including a grate, with a plurality of longitudinally extending ribs and a plurality of ribs that cross the longitudinally extending ribs, that defines a plurality of openings that face in different directions.

15. A surgical system as claimed in claim 14, wherein the arm comprises a flexible articulating arm.

16. A surgical system as claimed in claim 15, wherein the flexible articulating arm includes a plurality of links and a tension cable.

17. A surgical system as claimed in claim 14, wherein
the arm includes a first connector;
the retractor includes a second connector; and
the first and second connectors are configured to releasably connect the retractor to the arm.

18. A surgical system as claimed in claim 14, wherein the fluid port is carried by and extends longitudinally along tissue contact side of the blade.

19. A surgical system as claimed in claim 14, further comprising:
a fluid tube; and
a connector tube having a first end connected to the fluid tube and second end associated with the fluid port.

20. A surgical system as claimed in claim 14, wherein the blade is substantially rigid and flat.

21. A surgical system as claimed in claim 14, wherein
the blade include first and second blade members; and
the first and second blade members are movable relative to one another.

22. A surgical system as claimed in claim 21, wherein
the fluid port comprises a first fluid port associated with the first blade member and a second fluid port associated with the second blade member.

23. A surgical system as claimed in claim 14, further comprising:
at least one light emitting element carried by the blade.

24. A surgical system, comprising:
an arm; and
a retractor, operably connected to the arm, including a blade and a fluid port associated with the blade, the blade having a blade base, first and second blade members that are movable relative to one another, and first and second malleable rods that respectively connect the first and second blade members to the blade base.

25. A retractor apparatus, comprising:
a retractor including
a flat longitudinally extending blade having a tissue contact side, a second side opposite the tissue contact side, an outer perimeter that separates the tissue contact side from the second side, and first and second side edges that extend longitudinally along respective portions of the perimeter, and
a fluid port including a grate that extends outwardly from and longitudinally along the tissue contact side of the blade and is located inwardly of the first and second side edges; and
a connector associated with the retractor and configured to secure the retractor to a mechanical arm.

26. A retractor apparatus as claimed in claim 25, wherein
the blade includes distal and proximal longitudinal ends; and
the grate is associated with the distal longitudinal end and the connector is associated with the proximal longitudinal end.

27. A retractor apparatus as claimed in claim 25, wherein
the grate includes a plurality of longitudinally extending ribs and a plurality of ribs that cross the longitudinally extending ribs, that defines the openings.

28. A retractor apparatus as claimed in claim 25, further comprising:
a fluid tube; and
a connector tube having a first end connected to the fluid tube and second end associated with the fluid port.

29. A retractor apparatus as claimed in claim 25, wherein the blade is substantially rigid.

* * * * *